United States Patent [19]

Pews et al.

[11] Patent Number: 5,091,580
[45] Date of Patent: Feb. 25, 1992

[54] PROCESS FOR THE PREPARATION OF 2,6-DIFLUOROANILINE

[75] Inventors: R. Garth Pews, Midland; James A. Gall, Sanford, both of Mich.

[73] Assignee: DowElanco, Indianapolis, Ind.

[21] Appl. No.: 676,017

[22] Filed: Mar. 27, 1991

[51] Int. Cl.$^5$ ............................................ C07C 209/26
[52] U.S. Cl. .................................... 564/407; 570/143; 570/147
[58] Field of Search ................. 564/407; 570/147, 143

[56] References Cited

U.S. PATENT DOCUMENTS

| | | | |
|---|---|---|---|
| 3,057,922 | 10/1962 | Luvisi et al. | 564/407 |
| 3,376,345 | 4/1968 | Fielding et al. | 564/407 |
| 4,197,259 | 4/1980 | Guzik | 564/407 |
| 4,918,251 | 4/1990 | Halvachs | 570/143 |
| 4,937,397 | 6/1990 | Pews et al. | 570/147 |

OTHER PUBLICATIONS

Florin et al., "Reactions of Aromatic Fluorocarbons with Hydrogen", Journal of Research of National Bureau of Research, vol. 62, No. 3, Mar. 1959, p. 119.
J. Fluorine Chem., 2, 19 (1972/73), R. H. Shiley et al.
Doklady Akad. Nauk S.S.R., 127, 1225 (1959), N. N. Vorozhtsov.

*Primary Examiner*—Marianne Cintins
*Assistant Examiner*—Jessica H. Nguyen
*Attorney, Agent, or Firm*—Craig E. Mixan; Ronald G. Brookens

[57] ABSTRACT

2,6-Difluoroaniline is prepared from 1,2,3-trichlorobenzene by partial fluorine exchange to a mixture of 2,6-difluorochlorobenzene and 2,3-difluorochlorobenzene, amination of the chloro substituents, and separation of the desired product from the isomeric 2,3-difluoroaniline. By incorporating a selective reduction into the process immediately after the partial fluorine exchange, the undesirable 2,3-difluorochlorobenzene is converted into valuable ortho-difluorobenzene and the 2,3-difluoroaniline isomer is avoided.

3 Claims, No Drawings

PROCESS FOR THE PREPARATION OF 2,6-DIFLUOROANILINE

FIELD OF INVENTION

The present invention concerns a process for preparing 2,6-difluoroaniline from 1,2,3-trichlorobenzene. The process is characterized by the steps of partial fluorine exchange, amination and separation of the isomeric mixture containing the product. Alternatively, the process can be characterized by the steps of partial fluorine exchange, selective reduction, amination and separation.

BACKGROUND OF THE INVENTION 2,6-Difluoroaniline is useful as an intermediate in the manufacture of a variety of chemical products including, for example, dyes, pharmaceuticals and agricultural chemicals, and is presently manufactured in a multistep process involving the following reaction sequence:

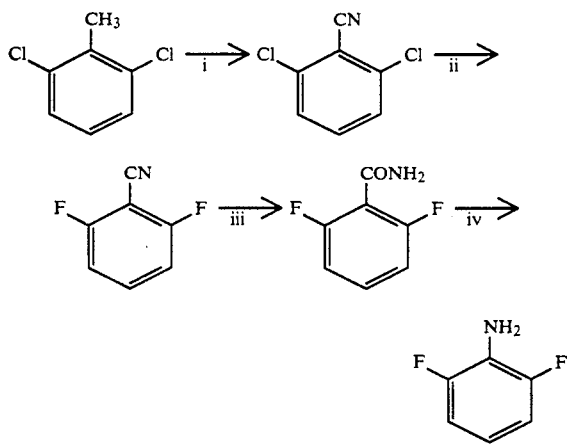

i) ammoxidation of 2,6-dichlorotoluene to 2,6-dichlorobenzonitrile;
ii) halogen-exchange to 2,6-difluorobenzonitrile;
iii) hydration to 2,6-difluorobenzamide; and
iv) Hoffman rearrangement to 2,6-difluoroaniline.

In addition, 2,6-dichlorotoluene itself is not readily available. Thus, as a result of the complexities of the chemistry, although commercially available, 2,6-difluoroaniline is quite expensive.

Alternative technologies have been suggested to manufacture 2,6-difluoroaniline, but they also have serious drawbacks. For example, fluorinated aromatics are often prepared by diazonium chemistry in which an amino moiety is transformed into a fluorine substituent by reaction with nitrous acid to form a diazonium salt and subsequent decomposition of the diazonium salt in the presence of fluoride. However, diazonium salts are unstable and the decomposition reaction is highly exothermic. In addition, the decompositions are generally conducted in highly reactive and corrosive anhydrous hydrofluoric acid.

Alternatively, 2,6-difluoroaniline has also been prepared via lithiation of 1,3-difluorobenzene followed by carbonation to the carboxylic acid and conversion of the acid moiety to the amine with hydrazoic acid (see British Patent 1,080,167). Unfortunately, neither lithiation nor hydrazoic acid lend themselves to large scale use.

More recently, 2,6-difluoroaniline has been prepared from 1-chloro-3,5-difluorobenzene by the following reaction scheme:

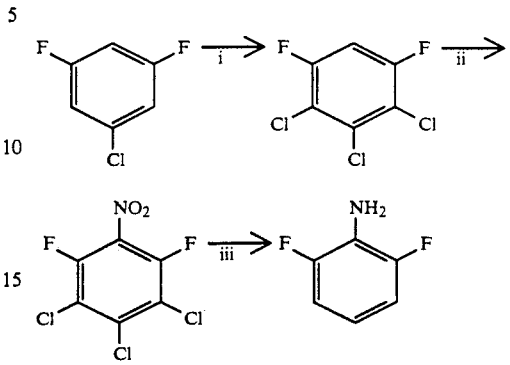

i) chlorination of 1-chloro-3,5-difluorobenzene to 4,6-difluoro-1,2,3-trichlorobenzene;
ii) nitration to 2,6 -difluoro-3,4,5-trichloronitrobenzene; and
iii) reduction to 2,6-difluoroaniline.

Unfortunately, 3,5-difluorochlorobenzene is not commercially available on a large scale; nor is the 1,3,5-trichlorobenzene from which it can most conveniently be prepared.

Thus, it is desirable to have a process for safely and economically producing 2,6-difluoroaniline in good yield from commercially available starting materials.

SUMMARY OF THE INVENTION

The present invention concerns a process for preparing 2,6-difluoroaniline from 1,2,3-trichlorobenzene by the following reaction scheme:

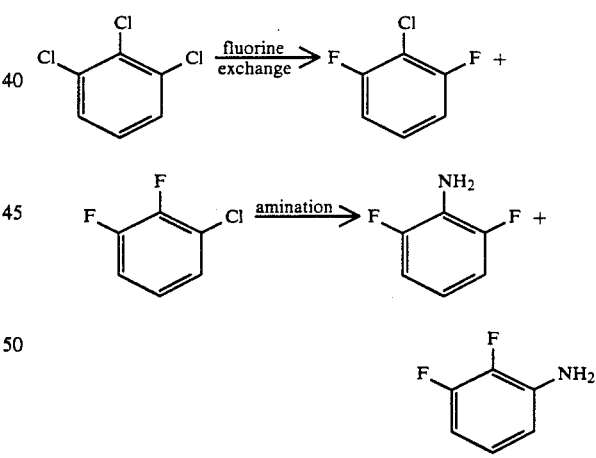

According to the present invention, the process is comprised of the following steps:
(a) exchanging two chlorines from 1,2,3-trichlorobenzene with fluorines to give a mixture of 2,6-difluorochlorobenzene and 2,3-difluorochlorobenzene;
(b) aminating the mixture of difluorochlorobenzenes to give a mixture of 2,6-difluoroaniline and 2,3-difluoroaniline; and
(c) separating the 2,6-difluoroaniline from the mixture.

Alternatively, the present invention also concerns a process for preparing 2,6-difluoroaniline from 1,2,3-trichlorobenzene by the following reaction scheme:

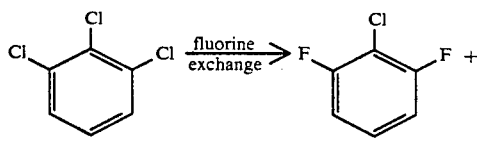

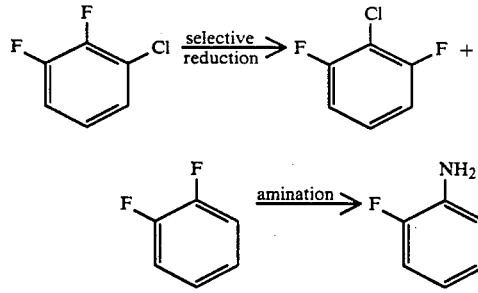

This alternative process is comprised of the following steps:
(a) exchanging two chlorines from 1,2,3-trichlorobenzene with fluorines to give a mixture of 2,6-difluorochlorobenzene and 2,3-difluorochlorobenzene;
(b) selectively reducing the chlorine from the 2,3-difluorochlorobenzene to give a mixture of 2,6-difluorochlorobenzene and ortho-difluorobenzene;
(c) separating the ortho-difluorobenzene from the mixture; and
(d) aminating the 2,6-difluorochlorobenzene to give 2,6-difluoroaniline.

The separation of the ortho-difluorobenzene (step (c)) and the amination (step (d)) can be conducted in either order.

By conducting the partial fluorine exchange and amination consecutively, 2,6-difluoroaniline can be prepared from a readily available and relatively inexpensive starting material, i.e., 1,2,3-trichlorobenzene, and can be separated from isomeric products at the aniline stage with relative ease. In addition, by incorporating a selective reduction into the process between the partial fluorine exchange and amination, a valuable by-product, ortho-difluorobenzene, can also be recovered from the process.

DETAILED DESCRIPTION OF THE INVENTION

The partial fluorine exchange is typically accomplished by the action of fluoride ion on 1,2,3-trichlorobenzene. The conversion of 1,2,3-trichlorobenzene to a mixture of 2,6-difluorochlorobenzene and 2,3-difluorochlorobenzene is a stepwise process which produces a mixture of products.

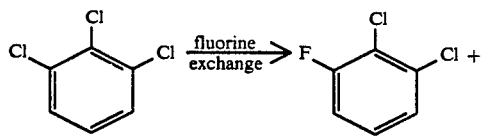

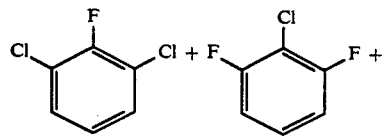

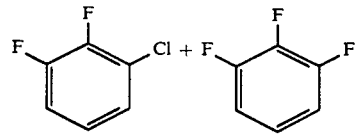

Those components of the mixture with different degrees of fluorine content, e.g., one fluorine as opposed to two fluorines, are usually easily separated from one another by distillation. Those components having the same fluorine content, on the other hand, oftentimes have very similar boiling points and are difficult to separate by distillation. Although the difluorochlorobenzenes can be easily separated from the other components of the mixture by distillation, they cannot be so easily separated from one another. Thus, it is most convenient to conduct the desired separation of isomers later in the process.

The fluorine exchange reaction is effectively conducted by contacting the 1,2,3-trichlorobenzene with an effective amount of KF or CsF under substantially anhydrous conditions in a suitable polar aprotic solvent at a temperature so that fluorine exchange readily occurs.

KF and CsF, which are the usual fluorinating agents employed, are commercially available compounds. Substantially anhydrous and finely-divided KF or CsF are preferred. Amorphous or spray-dried forms are particularly preferred. Substantially anhydrous KF and CsF can be prepared, for example, by drying in vacuo at 140°-250° C. for several hours.

Suitable polar aprotic diluents include N-methyl pyrrolidinone (NMP), N-cyclohexyl pyrrolidinone (NCHP), 1,3-dimethyl-2-imidazolidinone (DMI) and 1,3-dimethyl-3,4,5,6-tetrahydro-2-(1H)pyrimidone (DMTHP).

The fluorine exchange is conducted under substantially anhydrous conditions at elevated temperatures of from about 170° to about 290° C. Preferred temperature ranges are from about 200° to about 250° C. when CsF is used, and from about 250° to about 290° C. when KF is used.

Pressures of from atmospheric to greater than atmospheric are typically employed. For CsF, which is more reactive than KF, it is often convenient to operate at atmospheric pressure. For KF, which is less expensive than but also less reactive than CsF, it is preferred to operate at the autogenous pressure generated by the diluent, starting material and product in a sealed reactor at the preferred reaction temperatures of 250° to 290° C. Such pressures typically range from slightly above atmospheric to about 500 pounds per square inch gauge (psig) and depend upon the volume of the reactor. Optionally, the reaction can be run under pressure in a suitably designed reactor equipped with a distillation column so the product can be removed as formed.

Water is detrimental to the reaction and substantially anhydrous reaction conditions are preferred. By substantially anhydrous is meant that the reaction medium contains less than about 500 parts per million (ppm) water. Preferably the reaction medium contains less than about 150 ppm water. Substantially anhydrous conditions may be achieved employing standard drying techniques. For example, a typical laboratory reactor can be dried by distilling the polar aprotic solvent under a vacuum before addition of the reactants. Optionally, a small amount (5-10 percent by weight of the polar aprotic solvent) of a non-polar solvent such as an aromatic hydrocarbon (toluene, xylene, etc.) may be added to the polar aprotic solvent to aid in the removal of water by azeotropic distillation. Residual water in the reactor system is also often removed by azeotropic distillation.

The amount of polar aprotic solvent is not critical, but it is advantageous to employ enough solvent to keep the starting material in solution at reaction temperatures, generally from about 2 to about 25 parts by weight of the solvent per part by weight of the 1,2,3-trichlorobenzene. The reaction consumes the reactants in the ratio of one mole of fluorinating agent per mole of exchangeable chlorine atoms present in the starting material. Since a mixture of difluorochlorobenzenes is desired, about 2 molar equivalents of KF or CsF per mole of starting material are consumed. However, since very little trifluorobenzene is formed in the exchange, an excess of fluorinating agent is beneficial. Optionally, the difluorochloro isomers can be removed from the reactor by distillation as they are formed, thereby eliminating formation of 1,2,3-trifluorobenzene. Usually from about 3.0 to about 4.0 moles of KF or CsF are employed per mole of 1,2,3-trichlorobenzene.

In carrying out the fluorine exchange, usually the solvent and fluorinating agent are added to an appropriate reaction vessel, and the reaction is dried by distilling a small portion of the solvent. The starting material is then added to the reaction vessel, and the reaction mixture is heated to a temperature high enough to maintain a satisfactory reaction rate. The product may be recovered from the reaction mixture after completion of the reaction by extraction or by flash distillation. The desired difluorochlorobenzene fraction of the reaction mixture can conveniently be isolated by distillation.

The amination is usually performed by contacting the difluorochlorobenzene with concentrated ammonium hydroxide in the presence of a copper-containing catalyst. The chloro substituent is selectively replaced by an amino group. Suitable catalysts include, for example, the oxide, hydroxide, chloride, bromide, iodide, sulfate and acetate salts of copper in either its cuprous ($+1$) or cupric ($+2$) oxidation state. In terms of conversions and accountability of raw materials, the preferred catalyst is cuprous oxide. The copper-containing catalyst is usually employed in an amount corresponding to from about 0.01 to about 0.25 moles of catalyst per mole of difluorochlorobenzene; from about 0.02 to about 0.10 moles of catalyst per mole of difluorochlorobenzene is preferred.

While the exact concentration and amount of ammonium hydroxide used in the present invention is not critical, it is advantageous to use an amount of $NH_4OH$ in excess of the stoichiometric amount needed to react with the difluorochlorobenzene present. In fact, concentrated $NH_4OH$ is conveniently used as both the solvent and reactant.

The present reaction is conducted at elevated temperatures of from about 100° to about 200° C. The preferred temperature range is from about 130° to about 170° C.

Because the reaction temperatures are above the boiling point of concentrated $NH_4OH$, the reaction is conducted at pressures at least as great as the autogenous pressure of the mixture of materials at the prescribed temperature, i.e., at pressures sufficient to maintain the $NH_4OH$ in the reaction mixture substantially in the liquid phase. Such pressures typically range from slightly above atmospheric to about 700 pounds per square inch gauge (psig) and depend upon the volume of the reactor.

In carrying out the amination, the difluorochlorobenzene, ammonium hydroxide and copper salt are added to a pressure reactor which is then sealed. The reaction is run at the prescribed temperature to the desired stage of completion at which point the reactor is cooled and carefully opened.

The reaction is preferably run to less than complete conversion to minimize by-products. The difluoroaniline can be recovered from the reaction mixture by conventional techniques such as extraction or distillation. The isomeric 2,6- and 2,3-difluoroanilines can be separated by fractional distillation. Unreacted difluorochlorobenzene can be recovered by similar techniques and recycled.

In the reduction step, the mixture of 2,6-difluorochlorobenzene and 2,3-difluorochlorobenzene is contacted with a hydrogen source in the presence of a palladium catalyst. During the course of the reaction, the chloro group of the 2,3-difluorochlorobenzene is preferentially removed.

The selective reduction is fairly specific to palladium catalysts, and palladium on carbon has generally been found to be more effective than palladium dispersed on other supports. Thus, the most preferred catalysts range from about 0.5 to about 10 weight percent palladium on carbon. Generally, from about 0.01 to about 0.20 parts of palladium are employed per part of difluorochlorobenzene; from about 0.01 to about 0.10 parts are preferred.

The reduction can be conducted using hydrogen gas as the hydrogen source. The hydrogen gas can be continuously sparged into the reaction mixture at atmospheric pressure or the reaction mixture can be pressurized with hydrogen gas in a sealed reactor. With hydrogen gas, however, it is sometimes difficult to control the extent of reduction.

Formate salts are often convenient hydrogen sources. By the term "formate salts" is meant alkali metal formates, such as sodium formate and potassium formate, ammonium formate and trialkylammonium formates wherein the alkyl groups are straight-chained alkyl groups of 1 to 4 carbons, such as triethylammonium formate. The trialkylammonium formates, being relatively non-hygroscopic, easily prepared and quite soluble in most organic solvents, are among the preferred formate salts.

The trialkylammonium formates can be prepared by stirring an excess of trialkylamine with formic acid in toluene. Removal of the solvent and excess amine by distillation leaves the trialkylammonium formate as a residue which can then be diluted with the desired solvent to give a reagent solution of known concentration. As an alternative to preforming the trialkylammonium formate solution, this reagent can be prepared in situ by the addition of a stoichiometric excess of trialkylamine to 96 percent formic acid in conjunction with the palladium catalyst during the reduction in a fashion similar to that described by Cortese et al., *J. Org. Chem.*, 42, 3491 (1977).

The reduction is typically performed using near stoichiometric amounts of reagents. Thus, from 0.9 to 1.1 equivalents of hydrogen source are usually employed for each equivalent of substrate to be reduced. However, for more sluggish reactions a greater than 10 percent excess of the hydrogen source can be tolerated without forfeiture of selectivity.

The reduction is generally performed in an organic solvent that is inert to the reaction conditions. Aliphatic nitriles and aliphatic alcohols and aromatic hydrocarbons are particularly preferred. With respect to the nitriles, acetonitrile is most preferred. With respect to the alcohols, $C_2$ to $C_4$ alcohols and glycols are preferred. 2-Propanol and ethylene glycol are particularly preferred for those reactions using an alkali metal formate as the hydrogen source. With respect to aromatic hydrocarbons, toluene is preferred. Aromatic hydrocarbons are acceptable solvents for the trialkylammonium formates but are unacceptable for the alkali metal formates, which are essentially insoluble in this class of solvents.

The reduction is generally carried out at a temperature from about ambient to about 150° C., preferably from ambient to about 100° C. Operating pressures are not critical and may vary from atmospheric pressure to about 700 pounds per square inch gauge (psig). Pressures from atmospheric to about 200 psig are preferred.

Since the reduction of the aromatic chlorines produces hydrogen chloride, at least one equivalent of an HCl acceptor should be added for each chlorine reduced to buffer the system. Such buffers can include, for example, alkali metal carbonates and acetates or organic amines such as pyridine, alkylamines or alkanolamines.

In a typical reduction reaction the mixture of 2,6-difluorochlorobenzene and 2,3-difluorochlorobenzene is introduced into a pressure reactor along with a solvent and a palladium on carbon catalyst. The reactor is sealed, pressurized with hydrogen and stirred at about 100° C. until the chloro substituent has been removed from the 2,3-difluorochlorobenzene. After cooling and venting, the reaction mixture can be isolated by conventional procedures such as filtration and extraction. The ortho-difluorobenzene can be separated from the 2,6-difluorochlorobenzene by distillation, or the mixture can be aminated as described hereinabove and the ortho-difluorobenzene can be separated from the 2,6-difluoroaniline by distillation.

The following examples are presented to illustrate the invention and should not be construed as limiting the scope of the invention. All melting points and boiling points are uncorrected.

EXAMPLE 1

Partial Fluorine Exchange Reaction

A 600 milliliter (mL) Hastelloy C Pressure reactor was charged with 58 grams (g) (1.0 mol) of KF, 350 mL of N-methyl pyrrolidinone (NMP) and 45.4 g (0.25 mol) of 1,2,3-trichlorobenzene. The reactor was sealed and pressure tested. The reaction mixture was stirred at 270° C. for 24 hours (hr). After cooling and venting the reactor, the reaction mixture was analyzed by gas chromatography (GC) using an internal standard method. The analysis indicated the following composition: 1,2,3-trichlorobenzene (TCB; 10 percent), dichlorofluorobenzenes ($Cl_2FB$; 48 percent), difluorochlorobenzenes ($ClF_2B$; 22 percent) and 1,2,3-trifluorobenzene (TFB; <1 percent). The aromatics were flash distilled from the mixture and the distillate was redistilled on a spinning band column. The difluorochlorobenzene fraction had a boiling point of 134°–138° C. The dichlorofluorobenzene fraction had a boiling point of 172°–178° C.

EXAMPLE 2

A series of KF exchanges was conducted following the general procedures of Example 1. The experimental conditions and results of these experiments are summarized in Table 1.

TABLE 1

KF Exchange on 1,2,3-Trichlorobenzene

| Solvent | mol TCB | KF | T (°C.) | T (hr) | mol % TCB | ClF$_2$B | Cl$_2$FB | TFB |
|---|---|---|---|---|---|---|---|---|
| DMTHP | 0.25 | 1.0 | 270 | 24 | 4 | 32 | 40 | <1 |
| DMTHP | 0.25 | 1.0 | 280 | 12 | 4–8 | 28–38 | 40–46 | ~1 |
| DMTHP | 0.25 | 1.0 | 290 | 12 | 1 | 40 | 22 | ~1 |
| DMI | 0.25 | 1.0 | 270 | 24 | 4 | 34 | 42 | <1 |
| DMI | 0.25 | 1.0 | 280 | 18 | 2 | 42 | 34 | 2 |
| DMI | 0.25 | 1.0 | 280 | 30 | 1 | 34 | 18 | 2 |
| NMP | 0.25 | 1.0 | 280 | 18 | 6 | 27 | 40 | ~1 |
| NMP | 0.25 | 1.0 | 290 | 12 | 4 | 30 | 38 | 1.5 |
| DMI | 0.50 | 1.0 | 290 | 12 | 3–4 | 35–38 | 39–40 | 1 |

DMTHP - 1,3-dimethyl-3,4,5,6-tetrahydro-2-(1H)pyrimidone
DMI - 1,3-dimethyl-2-imidazolidinone
NMP - N-methyl pyrrolidinone

EXAMPLE 3

A 600 mL Hastelloy C pressure reactor was charged with 152 g (1.0 mol) of CsF, 350 mL of 1,3-dimethyl-2-imidazolidinone (DMI) and 90.8 g (0.5 mol) of 1,2,3-trichlorobenzene. The reactor was sealed and pressure tested. The reaction mixture was stirred at 250° C. for 12 hr. After cooling and venting the reactor, the reaction mixture was analyzed by gc using an internal standard method: TCB (<1 percent), Cl$_2$FB (32 percent), CF$_2$B (62 percent) and TFB (3 percent).

EXAMPLE 4

To a 2000 mL 4-necked nickel flask equipped with a mechanical stirrer and a 15 tray vacuum-jacketed Oldershaw column was added 953 mL of DMI. Approximately 5 g of solvent was removed by distillation (150 tor) to dry the system. The vacuum was released with nitrogen and 271 g (1.5 mol) of 1,2,3-trichlorobenzene and 608 g (4.0 mol) of finely ground CsF were added. The reaction mixture was stirred at 220° C. and reaction progress was monitored GC. After completion of the reaction (<2.5 percent starting material), 222 g of volatiles comprised of the following components were isolated as mixtures by distillation:

| | |
|---|---|
| 2,6-difluorochlorobenzene | 98.6 g |
| 2,3-difluorochlorobenzene | 68.9 g |
| 2,6-dichlorofluorobenzene | 20.3 g |
| 2,3-dichlorofluorobenzene | 20.4 g |
| 1,2,3-trifluorobenzene | 6.4 g |

EXAMPLE 5

Reduction Reaction

A 300 mL Hastelloy C pressure reactor was charged with 50 g (0.34 mol) of the difluorochlorobenzene isomers, 44.9 g (0.34 mol) of N-ethyldiethanolamine, ethylene glycol (125 mL) and 1.5 g of 10 percent Pd/C. The reactor was sealed, pressure tested with $N_2$ and pressured to 200 psig of $H_2$. The reaction mixture was stirred at 100° C. Additional $H_2$ was added until hydrogen uptake was complete. Reaction time was ~12 hrs. After cooling, the reactor was vented and opened and the catalyst was filtered from the solution. The reaction solution was distilled on a Nester-Faust spinning band distillation column to give o-difluorobenzene (bp 90°-92° C.) and 2,6-difluorochlorobenzene (bp 134°-138° C.).

EXAMPLE 6

Amination Reaction

A 300 mL Hastelloy C pressure reactor was charged with 0.096 mol of a mixture of difluorochlorobenzenes obtained according to Examples 1-3, cuprous oxide (0.009 mol) and 100 mL of concentrated (28 percent) $NH_4OH$. The reactor was sealed and pressure tested. The reaction mixture was stirred at 160° C. for 24 hr. After cooling and venting the reactor, the reaction mixture was filtered to remove solid catalyst and the product was isolated by continuous extraction with methylene chloride overnight. Analysis by GC using an internal standard method indicated the following composition: difluorochlorobenzenes ($ClF_2B$; 10 percent), 2,6-difluoroaniline (2,6-DFA; 39 percent), 2,3-difluoroaniline (2,3-DFA; 27 percent) and chlorofluoroanilines (CFA; 4 percent).

After removal of the methylene chloride on a rotoevaporator, the residue was distilled on a Nester-Faust spinning band distillation column. After removal of unreacted difluorochlorobenzene isomers, 2,6-difluoroaniline (bp 152°-154° C.) was collected. The purity by GC analysis was 99 percent. Further distillation gave 2,3-difluoroaniline (bp 169°-172° C.). The purity by GC analysis was 96 percent. The IR spectra were identical to authentic samples.

EXAMPLE 7

A series of aminations was conducted following the general procedure of Example 6. The experimental conditions and results of these experiments are summarized in Table 2.

TABLE 2

Amination of Chlorodifluorobenzene

| $ClF_2B$ (Mol) | Catalyst (Mol %) | °C. | Hr | 2,6-DFA | 2,3-DFA | $ClF_2B$ | CFA |
|---|---|---|---|---|---|---|---|
| 0.093 | C (2) | 170 | 24 | 7 | 3 | 54 | 22 |
| 0.093 | C (5) | 170 | 24 | 14 | 9 | 53 | 9 |
| 0.093 | A (5) | 170 | 24 | 19 | 11 | 43 | 17 |
| 0.093 | A (10) | 170 | 24 | 32 | 25 | 3 | 3 |
| 0.093 | A (10) | 170 | 24 | 30 | 19 | 14 | 7 |
| 0.093 | B (2) | 170 | 24 | 22 | 14 | 29 | 12 |
| 0.093 | B (2) | 170 | 24 | 30 | 18 | 26 | 9 |
| 0.093 | B (5) | 170 | 24 | 33 | 24 | 7 | 7 |
| 0.093 | B (10) | 170 | 24 | 37 | 30 | 1 | 5 |
| 0.096 | B (10) | 160 | 24 | 35 | 23 | 21 | 4 |
| 0.192 | B (10) | 160 | 24 | 27 | 18 | 35 | 3 |
| 0.192 | B (10) | 160 | 24 | 27 | 18 | 35 | 2 |
| 0.096 | B (10) | 150 | 24 | 19 | 10 | 59 | 2 |
| 0.096 | B (10) | 150 | 24 | 21 | 10 | 52 | 3 |
| 0.096 | B (10) | 150 | 48 | 37 | 26 | 12 | 3 |
| 0.096 | B (10) | 140 | 24 | 10 | 6 | 72 | 2 |

A CuO
B $Cu_2O$
C $Cu_2SO_4 \cdot 5H_2O$

EXAMPLE 8

Preparation of 2,6-Difluoroaniline 2,6-Difluorochlorobenzene 13 g (0.088 mol), prepared as described in Example 5, 1.3 g (0.009 mol) $Cu_2O$ and 125 mL of concentrated ammonium hydroxide were charged to a 300 mL Hastelloy C Parr reactor. The reactor was sealed and pressure tested then heated and stirred at 160° C. for 42 hrs. After cooling and venting, the catalyst was filtered from the reactor mixture. After neutralization of the filtrate with concentrated HCl (with cooling) to pH ~7, the product was isolated from the aqueous phase by continuous extraction with methylene chloride. After removal of the methylene chloride, analyses gave the following compositions: starting material (15 percent), 2,6-difluoroaniline (71 percent), 2,6-diaminofluorobenzene (6 percent) and miscellaneous (8 percent). Distillation on a Nester-Faust spinning band column gave 2,6-difluoroaniline (bp 152°-154° C.) of 99 percent purity by GC analysis.

What is claimed is:

1. A process for preparing 2,6-difluoroaniline from 1,2,3-trichlorobenzene which comprises the following sequential steps:
   (a) exchanging two chlorines from 1,2,3-trichlorobenzene with fluorines under conditions which give a mixture of 2,6-difluorochlorobenzene and 2,3-difluorochlorobenzene;
   (b) selectively reducing the chlorine from the 2,3-difluorochlorobenzene in admixture with 2,6-difluorochlorobenzene by contacting the mixture with a hydrogen source in the presence of a palladium catalyst in an inert organic solvent from ambient temperature to about 150° C. to give a mixture of 2,6-difluorochlorobenzene and ortho-difluorobenzene;

(c) separating the ortho-difluorobenzene from the 2,6-difluorochlorobenzene; and (d) aminating the 2,6-difluorochlorobenzene under conditions which give 2,6-difluoroaniline.

2. A process for preparing 2,6-difluoroaniline from 1,2,3-trichlorobenzene which comprises the following sequential steps:

(a) exchanging two chlorines from 1,2,3-trichlorobenzene with fluorines under conditions which give a mixture of 2,6-difluorochlorobenzene and 2,3-difluorochlorobenzene;

(b) selectively reducing the chlorine from the 2,3-difluorochlorobenzene in admixture with 2,6-difluorochlorobenzene by contacting the mixture with a hydrogen source in the presence of a palladium catalyst in an inert organic solvent from ambient temperature to about 150° C. to give a mixture of 2,6-difluorochlorobenzene and ortho-difluorobenzene;

(c) aminating the mixture of 2,6-difluorobenzene and ortho-difluorobenzene under conditions which give a mixture of 2,6-difluoroaniline and ortho-difluorobenzene; and (d) separating the ortho-difluorobenzene and the 2,6-difluoroaniline from the reaction mixture and from each other.

3. A process for preparing ortho-difluorobenzene from 1,2,3-trichlorobenzene which comprises the following sequential steps:

(a) exchanging two chlorines from 1,2,3-trichlorobenzene with fluorines under conditions which give a mixture of 2,6-difluorochlorobenzene and 2,3-difluorochlorobenzene;

(b) selectively reducing the chlorine from the 2,3-difluorochlorobenzene in admixture with 2,6-difluorochlorobenzene by contacting the mixture with a hydrogen source in the presence of a palladium catalyst in an inert organic solvent from ambient temperature to about 150° C. to give a mixture of 2,6-difluorochlorobenzene and ortho-difluorobenzene;

(c) separating the ortho-difluorobenzene from the 2,6-difluorochlorobenzene.

* * * * *